(12) United States Patent
Zahouani et al.

(10) Patent No.: US 7,958,775 B2
(45) Date of Patent: Jun. 14, 2011

(54) TRIBOACOUSTIC PROBE

(75) Inventors: Hassan Zahouani, Besancon (FR); Roberto Vargiolu, Millery (FR); Alain Mavon, Corronsac (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 647 days.

(21) Appl. No.: 10/598,445

(22) PCT Filed: Mar. 4, 2004

(86) PCT No.: PCT/FR2005/000526
§ 371 (c)(1),
(2), (4) Date: Oct. 10, 2008

(87) PCT Pub. No.: WO2005/085805
PCT Pub. Date: Sep. 15, 2005

(65) Prior Publication Data
US 2009/0031791 A1 Feb. 5, 2009

(30) Foreign Application Priority Data
Mar. 4, 2004 (FR) .................................... 04 02283

(51) Int. Cl.
*G01N 19/02* (2006.01)
(52) U.S. Cl. .............................. 73/105; 73/9
(58) Field of Classification Search ............. 73/105, 73/9
See application file for complete search history.

(56) References Cited

U.S. PATENT DOCUMENTS

| 4,364,035 | A | 12/1982 | Kirsch |
| 4,390,873 | A | 6/1983 | Kirsch |
| 5,679,883 | A * | 10/1997 | Wedeven .......................... 73/10 |
| 5,795,990 | A * | 8/1998 | Gitis et al. ......................... 73/9 |
| 5,852,232 | A | 12/1998 | Samsavar et al. |
| 6,776,048 | B2 * | 8/2004 | Corrias et al. .................. 73/819 |
| 6,817,223 | B2 * | 11/2004 | Lenz ................................ 73/10 |
| 7,188,516 | B2 * | 3/2007 | Devlin et al. ............. 73/115.04 |
| 2002/0173223 | A1 | 11/2002 | Gitis et al. |

FOREIGN PATENT DOCUMENTS

| DE | 10 164044 | 7/2003 |
| FR | 28 11764 | 1/2002 |

OTHER PUBLICATIONS

"Biomedical micro-tribometer application for skin studies (both in vivo and in-vitro)", www.cetr.com/skin_testing.html., XP002293582, 12 pages, (Aug. 23, 2003).
Patton, et al., "Advanced tribometer for *in situ* studies of friction, wear and contact condition-Advanced tribometer for friction and wear studies", Tribology Letters, vol. 13, No. 4 pp. 263-273, (2002).

(Continued)

*Primary Examiner* — Jacques M Saint Surin
(74) *Attorney, Agent, or Firm* — Miller, Matthias & Hull, LLP

(57) ABSTRACT

The invention relates to a sensor for the quantitative measurement of the feel of a surface, comprising a prehensile envelope, a hollow contact body for bringing into contact with the surface on a sensing zone, first acoustic detection elements to detect noises emitted by the hollow body on contact with the sensing zone, second mechanical detection elements embodied for measurement of the normal pressure or the normal pressure and the rubbing force exerted by the surface on the hollow body. The above is of application in the measurement of the triboacoustic properties of the skin or phanera, textiles, leather, plastic materials or any other material for which the an appreciation of the feel thereof is important.

19 Claims, 3 Drawing Sheets

OTHER PUBLICATIONS

Lyon, "The Optical Mouse, and an Architectural Methodology for Smart Digital Sensors", VSL-81-1 Xerox Palo Alto Research Center, 19 pages, (Aug. 1981).

French Preliminary Search Report FR 0402283; report dated Aug. 24, 2004.
International Search Report PCT/FR2005/000526; report dated Aug. 3, 2005.

* cited by examiner

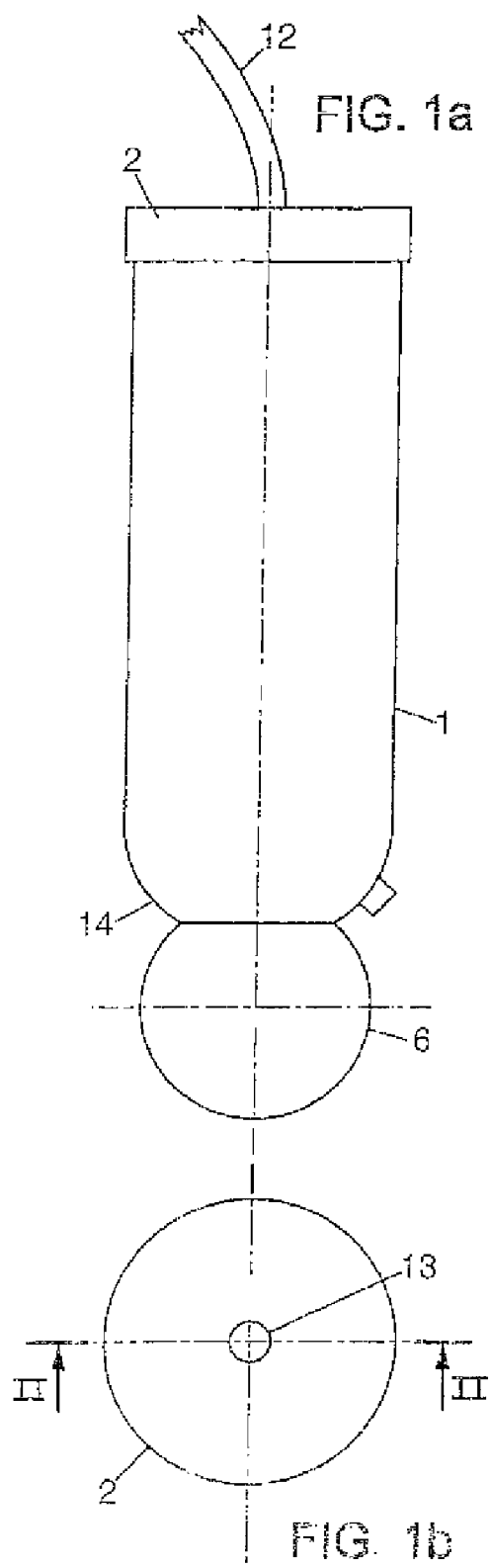
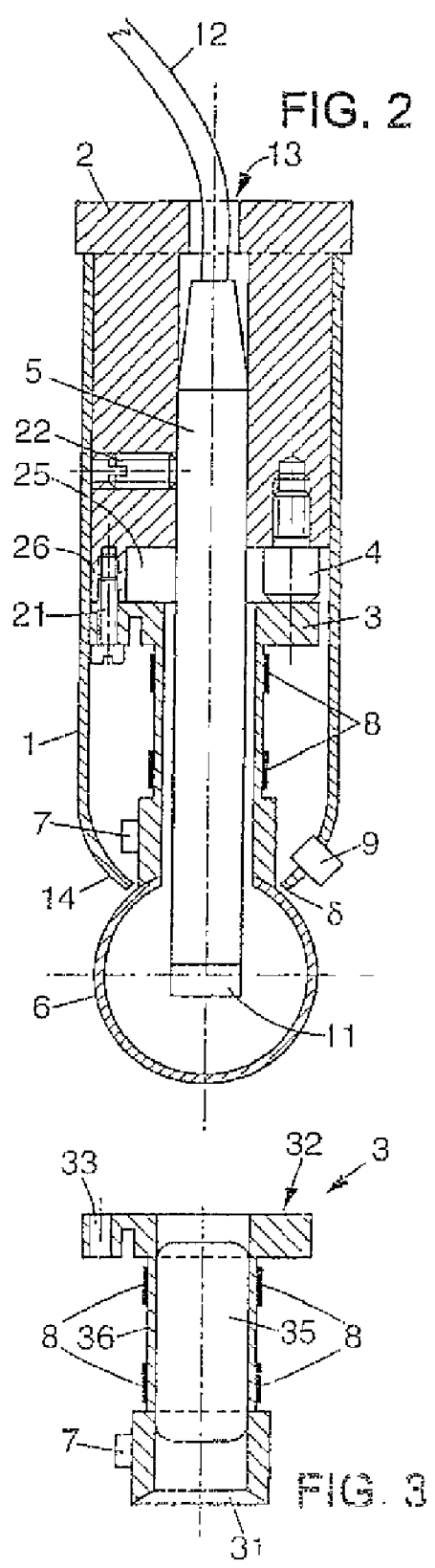

TRIBOACOUSTIC PROBE

FIELD OF THE DISCLOSURE

Background of the Disclosure

The present invention relates to the field of devices for measuring surface roughness. It relates more particularly to a probe for measuring the acoustic and tribological properties (called triboacoustic properties hereinafter) and thus to quantify the feel of a surface. It is applicable for measuring the triboacoustic properties of skin and phanera, tissues, leather, plastics, or any other material for which an appreciation of the feel is important.

The term "feel" is understood to mean the tactile qualities of a material, such as its softness, its firmness, its elasticity, its fineness, its resilience, and other qualities perceptible by the feel. This notion, for industrial requirements, is essentially measured by subjective tactile assessments based on panels. These are therefore experts who, after being trained, provide a qualitative assessment of the feel. This is especially the case when the impact in dermatology of a cream applied to the skin is to be evaluated.

These assessments correspond in fact to the in vivo evaluation of the tribological (contact, friction) properties and acoustic properties of the surface in question.

It will therefore be clearly understood that this approach is by nature random and highly subjective, as it remains very dependent on the expert.

The object of the present invention is to propose a probe for quantifying and characterizing the feel via the acquisition of physical data, such as static and dynamic friction forces, and soundwaves.

SUMMARY OF THE DISCLOSURE

For this purpose, the subject of the present invention is a probe for the quantitative measurement, of the feel of a surface, comprising:
  a prehensile casing;
  a hollow contacting body intended to be brought into contact, with the surface in a probed region;
  acoustic first detection elements for detecting noise emitted by the hollow body while it is in contact with the probed region; and
  mechanical second detection elements designed to measure the normal force and the friction force that are exerted by the surface on the hollow body.

Thus, the probe measures, by being scanned over the region of the body or surface to be studied, the mechanoacoustic behavior of this surface by quantifying specific parameters, Advantageously, the acoustic first detection elements comprise a microphone held inside the prehensile casing, this microphone comprising a membrane located inside the hollow body.

Moreover, the mechanical second detection elements comprise, respectively, at least one normal force sensor designed to measure the normal force and at least one friction force sensor designed to measure the friction force, which forces are experienced by the hollow body while it is in contact with the probed region.

In one preferred embodiment, the hollow body has a spherical shape. Advantageously, it is made in a material exhibiting excellent resonance capabilities, and a minimum rigidity, such as especially carbon fiber.

Other features and advantages of the invention will become more clearly apparent on reading the description that follows. This is purely illustrative and must be read in conjunction with the appended drawings in which:

BRIEF DESCRIPTION OF THE DRAWINGS

FIG. 1a is an overall view of one embodiment of the probe according to the invention;
FIG. 1b is a top view of the probe of FIG. 1a;
FIG. 2 is a sectional view on II-II of the probe of FIG. 1a;
FIG. 3 is a view of the elongate component intended to transmit the forces in the probe of FIGS. 1a, 1b and 2.

Figure 4:
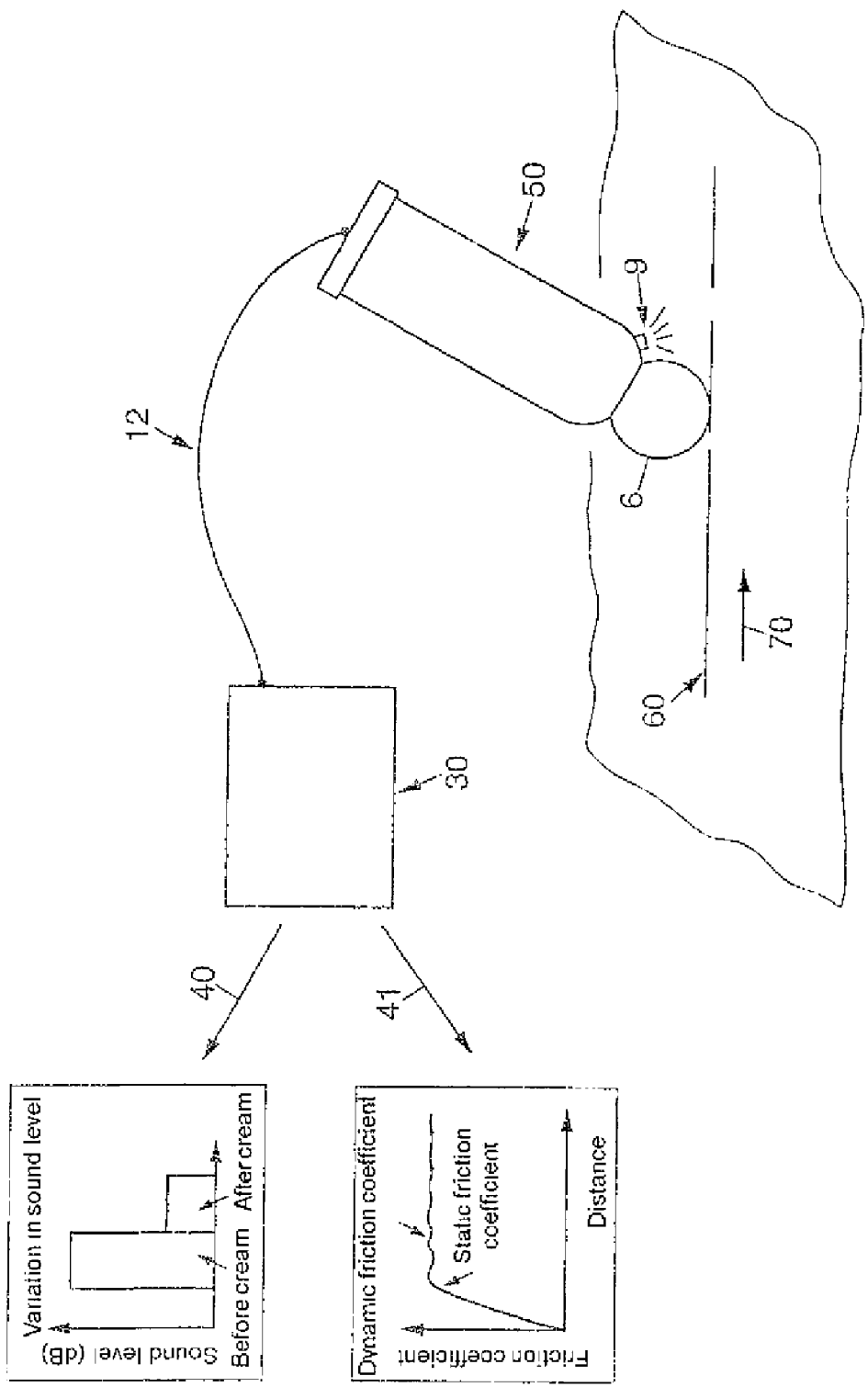
FIG. 4 is an overall view of the probe of FIG. 1 and of an electronic computing unit during a measurement on a surface.

One exemplary embodiment of a probe according to the invention is shown in FIGS. 1a and 1b.

DETAILED DESCRIPTION OF THE DISCLOSURE

The probe shown in FIG. 1a consists of an external casing 1, for example made of metal. It may be of cylindrical shape and elongate so as to be easily gripped by the operator, The external casing 1 is closed off at one of its ends by a retention body 2 that extends inside the external casing 1. Leading from the retention body 2, made of a metal alloy, are electrical wires 12 for data transmission to an electronic computing unit (not shown). At the other end 14 of the external casing 1 is the rubbing element 6 of the probe, intended to be applied to and moved over the surface to be analyzed. A laser diode 9 is placed close to the head of the external casing 1. This laser diode 9 allows a straight line segment to be traced, indicating the direction in which the probe is rubbed over the surface to be analyzed. Advantageously, the external casing 1 may be painted so as to minimize the surrounding noise.

FIG. 1b is a top view of the end of the probe on the side with the electrical wires 12, and it again shows the retention body 2 and the outlet 13 for the electrical wires 12 for transmitting data to the electronic computing unit.

FIG. 2 shows a sectional view on II-II of the probe shown in FIG. 1a. The retention body 2 has a cylindrical shape and matches the internal surface of the external casing 1. An opening is made inside the retention body 2 so that it can partly contain a microphone 5. This opening is extended in the outer-part of the retention body 2 by the outlet 13 provided for the electrical wires 12.

The microphone 5 is held in place inside the retention body 2 by a retaining screw 22 engaged in the retention body and clamped onto the microphone 5. The microphone 5 is of elongate shape, and its other end—the head of the microphone 11 having an acoustic vibrating membrane—is placed inside the rubbing element 6 which, in FIG. 2, appears as a hollow, and preferably spherical, body.

The hollow body 6 is fastened to an elongate component 3. This component 3 of shape elongate in the same direction as the casing 1 is fastened to the retention body 2 by means of a retaining screw 21 inside the external casing 1. The elongate component extends from the retention body 2 as far as the end 14 of the external casing 1. The length of the elongate component, 3 is such that a gap δ remains between the end 14 of the external casing 1 and the hollow body 6 fastened to the end of the elongate component. The elongate component 3 is preferably fixed to the retention body 2 only via one side. It is fastened to a projecting end 26 of the retention body 2, this end having a small area compared with the cross section of the retention body 2. In FIG. 2, a retaining screw 21 is shown, a second screw, symmetrical with respect to the plane of section, not being shown. A space 25 is left, between the elongate component 3 and the retention body 2 over most, of their facing areas. Thus, these two components can flex one with respect to the other, thanks to the space 25 and the small area of their fastening.

Placed in this space 25 is a normal force sensor 4, the fixed part of which is held in place on the retention body 2 and the moving part of which is in contact with the elongate component 3. This normal force sensor 4 is thus capable, while the probe is being moved over a surface to be studied, of detecting any normal force applied by the surface to be probed to the hollow body 6. This is because the gap δ between the hollow body 6 and the end 14 of the external casing 1, on the one hand, and the possible flexing between the elongate component 3 and the retention body 2 on the other hand, ensure that the normal force is transmitted from the surface to be probed to the moving part of the sensor 4.

An accelerometer 7 is placed laterally on the elongate component 3 near the hollow body 6. Strain gauges 8, of which there are four in FIG. 2, are fastened to the outer surface of the elongate component 3. The accelerometer 7 and the strain gauges 8 constitute sensors for sensing the friction force applied to the hollow body 6. The shape of the elongate component 3 and the gap δ allow this component to flex during movement of the hollow body 6 of the probe while in contact with the surface to be probed. Tangential movements of the hollow body relative to the external casing 1 are thus permitted. This flexure is measured directly by the accelerometer and the strain gauges 8.

Electrical wires (not shown) connect the various sensors to the electrical wires 12 for data transmission to an electronic computing unit.

An opening is made at the center of the elongate component 3 so as to let the body of the microphone 5 pass through it. This opening has a larger diameter than the external dimensions of the microphone so that the elongate component 3 does not come into contact with the body of the microphone during these deformations.

FIG. 3 shows the elongate component 3 provided with the strain gauges 8 and the accelerometer 7. It again shows the opening made at its center, along its axis, so as to let the body of the microphone pass through it. Two openings 35 are provided on either side of the elongate component along its long length, so that two plates 36 remain, these being formed on either side of the component 3. It is these plates 36 that, bear the strain gauges 8. The thickness of the plates 36 is calculated according to the characteristics of the constituent material of the component 3 and of the strain gauges 8. In the example shown in FIG. 3, each plate 36 bears two strain gauges. The component 3 is machined as a single part—it is recessed both at its center, in order to let the microphone body pass through it, and on the sides, in order to create the plates supporting the strain gauges. The openings 35 are preferably recessed so that the strain gauges 8 and the laser diode 9 of FIG. 2 lie substantially in the same plane. The flexure of the elongate component 3 is thus facilitated, thanks to the openings 35, while the rubbing element 6 is being moved over a surface to be analyzed, in the direction indicated by the laser diode 9.

Provided on one of the ends 31 of the elongate component is a conical hole intended for fastening the hollow body 6. On its opposite end, a thread 33 is provided for tightening the retaining screw 21 against the retention body 2. Diametrically opposite the thread 33, on this same end of the elongate component 3, is the bearing surface 32 in contact with the moving part of the normal force sensor 4. It is of course clearly possible to envisage the opposite case, in which the normal force sensor is fastened to the elongate component 3 and its moving part bears on the facing surface of the retention body 2.

The hollow body 6 constitutes the rubbing element of the probe. It contains free air and has to behave as a resonant box, so as to ensure good acoustic transmission of the noise resulting from the movement of the hollow body 6 over the surface to be analyzed. It must also be sufficiently rigid to transmit, the normal and friction forces while it is being moved over the surface to be probed. Materials of the carbon fiber type exhibit such characteristics. A table tennis ball, for example, constitutes an excellent rubbing element for a probe according to the invention.

Figure 5A:
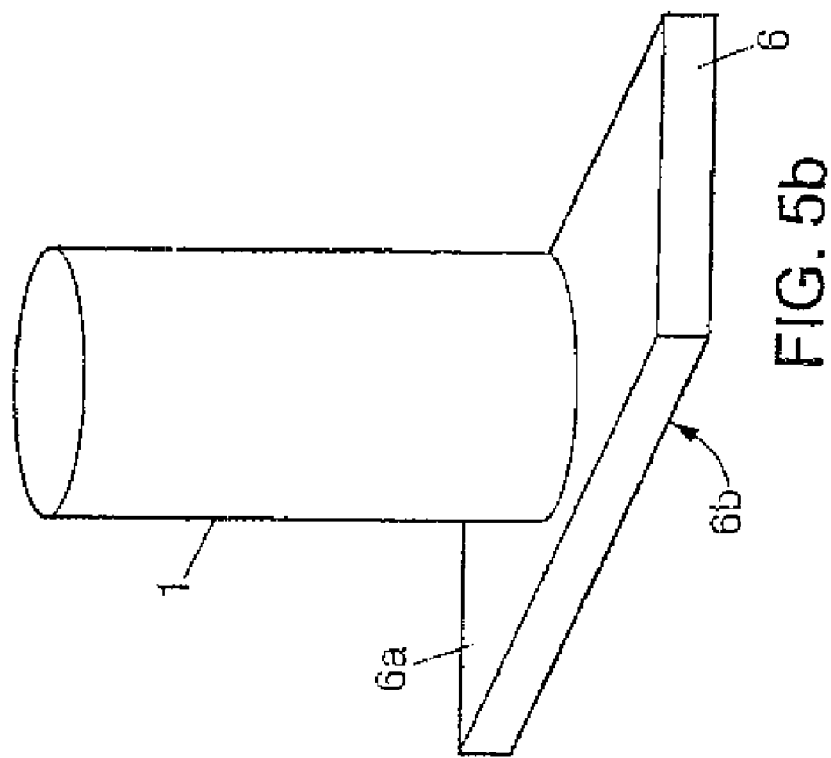
FIG. 5a is a diagram of the probe in a second embodiment.
Figure 5B:
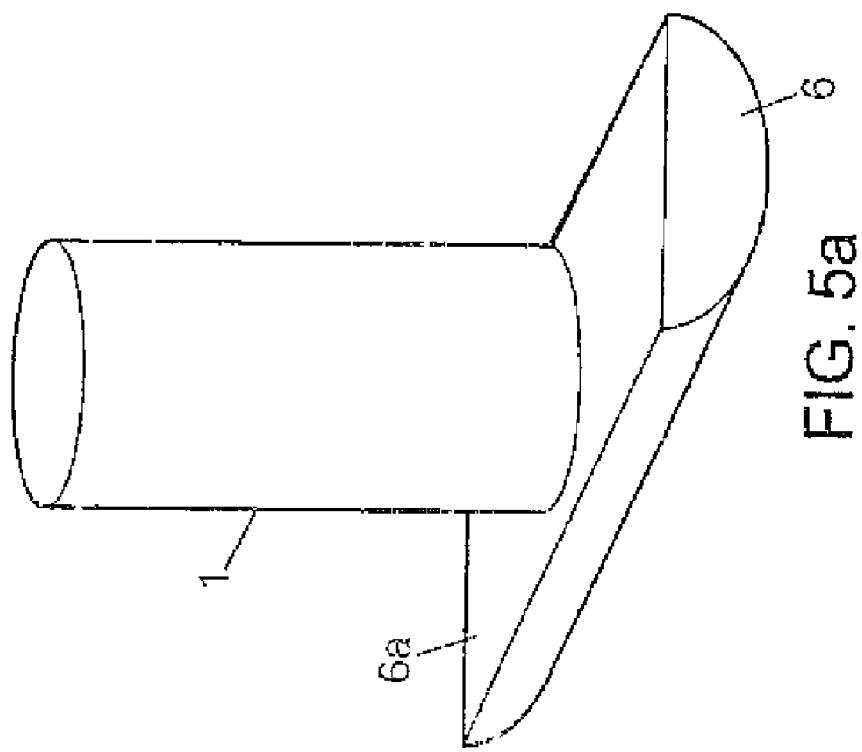
FIG. 5b is a diagram of the probe in a third embodiment.

FIGS. 5a and 5b show second and third embodiments of the probe according to the invention, respectively. The hollow body 6 has shapes that differ from the spherical shape of FIG. 1. In FIG. 1, the hollow body 6 has a plane upper part 6a, of substantially rectangular shape, and is fastened at its center to the elongate component 3 (not shown in FIG. 5a). The lower part 6b of the hollow body is formed by a cylinder portion. The hollow body 6 therefore has the shape of a cylinder portion resulting from cutting a cylinder in a plane parallel to its axis. The rounded part of the hollow body is the part intended to be brought into contact with the surface to be analyzed. For this type of hollow body, the probe is moved in a direction approximately perpendicular to the axis of the cylinder portion 6b. The contact surface, for contact between the hollow body and the surface to be analyzed, corresponds to a surface on the cylinder portion approximately parallel to the axis of the latter.

The hollow body shown in FIG. 5b is of approximately parallelepipedal shape, the upper surface 6a is of shape similar to that of FIG. 5a, and the hollow body is closed by a lower part 6b so as to form a parallelepiped with a lower surface 6c approximately parallel to the upper surface 6a. This hollow body offers a large area of contact with the surface to be analyzed.

The microphone is a conventional and commercially available microphone of elongate shape. It must have good acoustic capabilities. The microphone constitutes the acoustic first detection elements of the probe according to the invention.

The normal force sensor is a miniature force sensor capable of detecting forces from zero to a few newtons and of carrying out static and dynamic measurements. In another embodiment, especially for taking into account the various shapes that, the hollow body, as seen above, may adopt, the normal force sensor 4 may advantageously be replaced with a pressure sensor. The latter has the advantage of measuring the normal pressure exerted by the probed surface on the hollow body 6 independently of the shape of the hollow body. The pressure sensor is fitted in the same manner as the normal force sensor described above.

The strain gauges allow the static and almost static friction force to be determined, while the accelerometer makes it possible to obtain the dynamic component of this same force.

The normal and friction force sensors constitute mechanical second detection elements. The elongate component. 3 transmits the forces experienced by the hollow body 6 of FIGS. 1a and 1b to the mechanical second detection elements.

The probe according to the invention is particularly applicable for measuring the impact on the triboacoustic properties of a treatment applied to the probed surface. In cosmetology for example, the probe allows the impact of a moisturizing substance on the skin to be quantified by comparing the triboacoustic properties, recorded on a test, region of skin before any application, with the triboacoustic properties recorded on this same region at successive time intervals, after application of the moisturizing substance. Similar applications may be envisaged, for example by quantifying the impact of a shampoo on hair.

FIG. 4 shows an overall view of the probe and an electronic computing unit during its use for characterizing the feel of a surface 20. The operator (not shown in FIG. 4) brings the rubbing element 6 of the probe 50 into contact with the probed region of the surface 20 to be studied, and performs a linear rubbing scan on said surface in a direction 70 along a line 60. The laser diode 9, by tracing a straight line segment visible on the surface 20, allows the operator to easily follow the line 60 and the direction of movement 70. It also makes it possible, during successive passes along the line 60, to reposition the probe thanks to reference marks traced by the operator on the line 60.

In another embodiment, a device for measuring the speed of movement over the surface to be analyzed may be added to the probe. The laser diode 9 may be supplemented with an optical camera so as to a measurement device for determining the speed of movement of the probe over the surface to be analyzed. This technology is known from optical mouses. Such optical mouses are described in patents U.S. Pat. Nos. 4,364,035 and 4,390,873. Another optical mouse has been described in detail in the article *"The Optical Mouse And An Architectural Methodology For Smart Digital Sensors"* by Richard F. Lyon, VLSI-81-1 August 1981. This speed measurement makes it possible to control the speed of movement of the probe and thus ensure good calibration of the instrument. The operator can also control the speed of movement, of the probe. It is also possible to envisage correcting the measured values according to the speed of movement, in order to make the measurements independent of the user.

All the data recorded by the microphone on the one hand, and by the normal and friction force sensors on the other hand (and where appropriate by the speed measurement device when it is provided) is transmitted by the electrical transmission wires 12 to an electronic computing unit 30. The data obtained is then processed by complex computational algorithms, which make it possible to obtain simple parameters for quantifying the acoustic and tribological properties of the surface under study. The electronic unit 30 may also transmit, qualitative information of the sound type, associated with the amplitude of the data read, so that the operator can combine the calculated results with a subjective appreciation.

As regards the processing of the acoustic signal, during the linear rubbing scan along the line 60 by the operator, the noise is amplified by the resonant capabilities of the hollow body, and is picked up by a preamplifier mounted behind the diaphragm of the microphone (not shown in FIG. 4) in order to be converted into an electrical signal representative of the sound signal. The electrical transmission wires 12 convey the electrical signal thus picked up to the electronic computing unit 30.

The sound information shown in FIG. 4 may be processed, for example by a Fourier transform on the one hand, and by decomposition into continuous wavelets. A Fourier transform makes it possible to calculate the base spectral power density of the sound signal. It also makes it possible to take account of the multitude of physical and physiological phenomena involved at the interface between the rubbing element of the probe and the surface to be analyzed. It also makes it possible to obtain the mean sound level in decibels from the spectrum resulting from the transform, which has two advantages, namely that, of placing the measurements on a universally appreciable scale and of representing the scattered energy while the rubbing element is being rubbed over the surface to be analyzed. The continuous wavelet analysis itself allows the sound signal to be represented according to a time-frequency base.

These various parameters calculated from the sound signal make it possible to quantify and qualify in vivo the effect (retention, bioavailability, etc.) of the addition of active ingredients on surfaces such as, for example, skin or hair. A drop in sound levels may for example be detected, as shown by the graph 40 in FIG. 4, which levels are read after application of a repair cream to the skin.

As regards the processing of the information collected by the normal force (or normal pressure) sensor and the friction sensor, the electrical signals read are conveyed by the electrical transmission wires 12 to the electronic computing unit 30. These signals can then be converted by software into normal force and tangential force so as, for example, to calculate the change in the friction coefficient as a function of the movement.

By reading the normal force, or normal pressure, it is possible to control the various scans so as to ensure that the applied normal force is substantially the same during each pass over the surface to be analyzed. A scan along an analysis line 60 makes it possible to obtain a friction curve as a function of time, f(t) 41 shown in FIG. 4. The curve can be decomposed by an algorithm into three parts. The first is purely adhesive, in which the rubbing element of the probe exerts a stress that shears the material and starts the sliding. The second is a kind of relaxation, in which the movement is initiated, freeing the rubbing element from the grip of the surface forces. Finally, the last, is the dynamic phase in which the probe starts to move with slight, friction over the surface. Each of these curved parts can be characterized by a mechanical parameter, which are the stiffness (slope at the origin) and the static and dynamic friction coefficients. This analysis example is not limiting.

As specified above, the measurement, of the forces may be influenced by the speed with which the probe is scanned over the surface to be analyzed. This parameter, measured by the speed measurement device, may be taken into account in order to determine feel analysis values that are substantially independent of the scan speed and therefore independent of the user.

To give an example, the impact of a shampoo on the friction coefficient of hair may be measured as a function of the number of times it is washed.

The invention claimed is:

1. A probe for the quantitative measurement of the feel of a surface, comprising:
   a prehensile casing;
   a hollow contacting body intended to be brought into contact with said surface in a probed region;
   acoustic first detection elements for detecting noise emitted by said hollow body while it is in contact with said probed region; and
   mechanical second detection elements designed to measure either normal force or pressure and the fiction force that are exerted by said surface on said hollow body.

2. The probe as claimed in claim 1, wherein said acoustic first detection elements comprise a microphone held inside said prehensile casing, said microphone comprising a membrane located inside said hollow body.

3. The probe as claimed in, claim 1, wherein said mechanical second detection elements comprise at least one normal force sensor designed to measure the normal force experienced by said hollow body while it is in contact with said probed region.

4. The probe as claimed in claims 1, wherein said mechanical second detection elements comprise at least one normal pressure sensor designed to measure the normal pressure experienced by said hollow body while it is in contact with said probed region.

5. The probe as claimed in claim 1, wherein said mechanical second detection elements comprise at least one friction force sensor designed to measure friction force experienced by said hollow body while it is in contact with said probed region.

6. The probe as claimed in claim 1, which includes an elongate component extending between two ends, which component is held inside said prehensile casing and is connected at one of its ends to said hollow body, said component being designed to transmit the normal and friction forces to said second detection elements.

7. The probe as claimed in claim 6, wherein said friction force sensor comprises an accelerometer and strain gauges that are attached to said elongate component.

8. The probe as claimed in claim 7, wherein said elongate component includes two lateral openings so as to form two plates on either side of said elongate component, said plates bearing said strain gauges.

9. The probe as claimed in, claim 8 wherein said elongate component is formed from a metal alloy.

10. The probe as claimed in claim 1, which comprises a diode placed on said prehensile casing and intended to indicate the direction of movement of said probe while it is in contact with said probed region.

11. The probe as claimed in claim 10, wherein said diode is linked to an optical camera in order to form a device for measuring speed of movement of said hollow body over said probed region.

12. The probe as claimed in claim 1, wherein said hollow body has a spherical shape.

13. The probe as claimed in, claim 1, wherein said hollow body comprises a plane upper surface and a lower part consisting of a cylinder portion.

14. The probe as claimed in claim 1, wherein said hollow body comprises an upper surface and a lower surface that are plane and approximately parallel, said hollow body having a shape of a parallelepiped.

15. The probe as claimed in claim 1, wherein said hollow body is made of carbon fiber.

16. The probe as claimed in claim 1, which includes transmission elements for transmitting data from said first and second detection elements, and also from a speed measurement device, to an electronic computing unit.

17. The probe as claimed in the preceding claim, wherein said electronic computing unit is designed to convert said data into simple quantities for quantifying the feel of said probed region.

18. The probe as claimed in the preceding claim, wherein a gap is provided between said hollow body and said prehensile casing so as to allow normal and tangential movements of said hollow body.

19. The use of the probe as claimed in claim 1 for measuring the impact on the triboacoustic properties of a treatment applied to said probed surface.

* * * * *

UNITED STATES PATENT AND TRADEMARK OFFICE
CERTIFICATE OF CORRECTION

PATENT NO.        : 7,958,775 B2                                          Page 1 of 1
APPLICATION NO.   : 10/598445
DATED             : June 14, 2011
INVENTOR(S)       : Hassan Zahouani, Roberto Vargiolu and Alain Mavon It is certified that error appears in the above-identified patent and that said Letters Patent is hereby corrected as shown below:

On the Title Page, Item (22) "PCT Filed" should read:

March 4, 2005

Signed and Sealed this
Eighth Day of September, 2015

Michelle K. Lee
*Director of the United States Patent and Trademark Office*